United States Patent
Jabri et al.

(10) Patent No.: US 7,664,222 B2
(45) Date of Patent: Feb. 16, 2010

(54) PORTABLE DIGITAL TOMOSYNTHESIS IMAGING SYSTEM AND METHOD

(75) Inventors: Kadri Nizar Jabri, Waukesha, WI (US); Renuka Uppaluri, Pewaukee, WI (US); John Michael Sabol, Sussex, WI (US); Gopal Biligeri Avinash, Menomonee, WI (US)

(73) Assignee: General Electric Co., Schenectady, NY (US)

( * ) Notice: Subject to any disclaimer, the term of this patent is extended or adjusted under 35 U.S.C. 154(b) by 193 days.

(21) Appl. No.: 11/731,537

(22) Filed: Mar. 30, 2007

(65) Prior Publication Data
US 2008/0240343 A1  Oct. 2, 2008

(51) Int. Cl.
*G01N 23/00* (2006.01)
(52) U.S. Cl. .......................... 378/26; 378/21
(58) Field of Classification Search ............ 378/207, 378/21–27, 193–198, 205
See application file for complete search history.

(56) References Cited

U.S. PATENT DOCUMENTS

2002/0191744 A1* 12/2002 Mirabella ............... 378/102
2005/0226369 A1* 10/2005 Martin et al. ............. 378/22

* cited by examiner

*Primary Examiner*—Hoon Song
(74) *Attorney, Agent, or Firm*—Fletcher Yoder

(57) ABSTRACT

A portable tomosynthesis imaging system is disclosed that includes a portable X-ray source assembly and a portable detector assembly. The source assembly may be coupled to a portable power supply and controller such that multiple projection X-ray images may be obtained at a site that is not accessible by conventional tomosynthesis imaging systems. Image data may be transmitted from the detector by wired or wireless communication. Tomosynthesis image reconstruction may be performed locally at the portable system or remotely by the transmission of raw or filtered image data from the portable system. The portable system is particularly well-suited to field deployment, such as at accident scenes, scenes of natural or other disasters, or in confined clinical settings.

24 Claims, 4 Drawing Sheets

PORTABLE DIGITAL TOMOSYNTHESIS IMAGING SYSTEM AND METHOD

BACKGROUND

The present invention relates generally to digital tomosynthesis imaging systems, and more particularly to a portable tomosynthesis system suitable for use in on-sight locations, confined clinical environments, and so forth.

Digital X-ray tomosynthesis is an imaging technique that enables three-dimensional imaging of a patient using a large-area digital detector typically used for conventional (single projection) radiography. In clinical tomosynthesis techniques, a source of X-ray radiation is moved between imaging positions and multiple images are made by casting an X-ray beam on a digital detector. In certain applications, multiple, distributed and static X-ray sources may be used, or movable sources may be displaced in various patterns or trajectories. In certain systems, the detector is also moved during this process. Three-dimensional data is reconstructed in the form of a number of slices through the patient anatomy, each parallel to the detector plane. Tomosynthesis acquisition consists of a number of projections (X-ray exposures) covering an angular range of less than 180°, and typically between 20° and 40°.

Benefits of tomosynthesis imaging are well-known in practice and many applications have been clearly identified in which the technique is preferred over other medical imaging technologies and protocols. However, conventional clinical tomosynthesis systems require that the relative position of the X-ray source and the X-ray detector be known for each of the multiple exposures, so as to permit the appropriate reconstruction of the tomosynthesis slices. Although this may be a relatively straightforward requirement to satisfy in "fixed" digital radiography systems with dedicated mechanical positioners for both the source and the detector, such fixed systems cannot be readily moved or transported.

In certain situations, a "portable" tomosynthesis system would be an invaluable imaging technology. Such situations might include emergency medical applications, such as for rendering medical attention at the scenes of automobile accidents, trauma locations, building and natural disaster scenes, and so forth. In such situations, the person needing medical care normally should not be moved because of the risk of doing further damage to the spine or other tissues, particularly if a vertebral fracture or other internal injury may be present. Whereas a standard X-ray projection image may not be able to ascertain the presence of such fractures, reconstructed slice imaging from a portable tomosynthesis system should have much better capability for detecting the presence of absence of such fractures without moving the patient. Another use for a portable tomosynthesis system may be in small clinical settings where a larger footprint fixed digital radiography system would be impossible to accommodate given the space constraints.

At present, however, such portable tomosynthesis systems are not available. Difficulties in determining positions of the X-ray source and relative positions of the source and detector, among other technical hurdles, have made development and deployment of such systems problematic. There remains a need, however, for improved X-ray tomosynthesis systems that can be made portable and still provide reliable clinical images and data.

BRIEF DESCRIPTION

The present invention provides a portable tomosynthesis system and method designed to respond to such needs. The system may be used in a wide range of settings, including those discussed above. The system is based upon an X-ray source that is powered by a portable power supply and controller. The source may move on a known trajectory, or the source may include multiple distributed individual X-ray sources. A digital detector is associated with a source and is also portable. The detector may be wireless, and powered by a battery, or could also be powered by the same or a different power supply than the source. The source and detector need not be physically connected to one another for positioning. Positioning for determining the proper orientation of the source and detector during image acquisition may be performed in one of several ways, such as through the use of position sensing devices, such as electromagnetic transceivers. The system may thus be deployed easily and efficiently, and obtain image data which can be processed in accordance with conventional tomosynthesis imaging techniques.

DRAWINGS

These and other features, aspects, and advantages of the present invention will become better understood when the following detailed description is read with reference to the accompanying drawings in which like characters represent like parts throughout the drawings, wherein.

Figure 4:
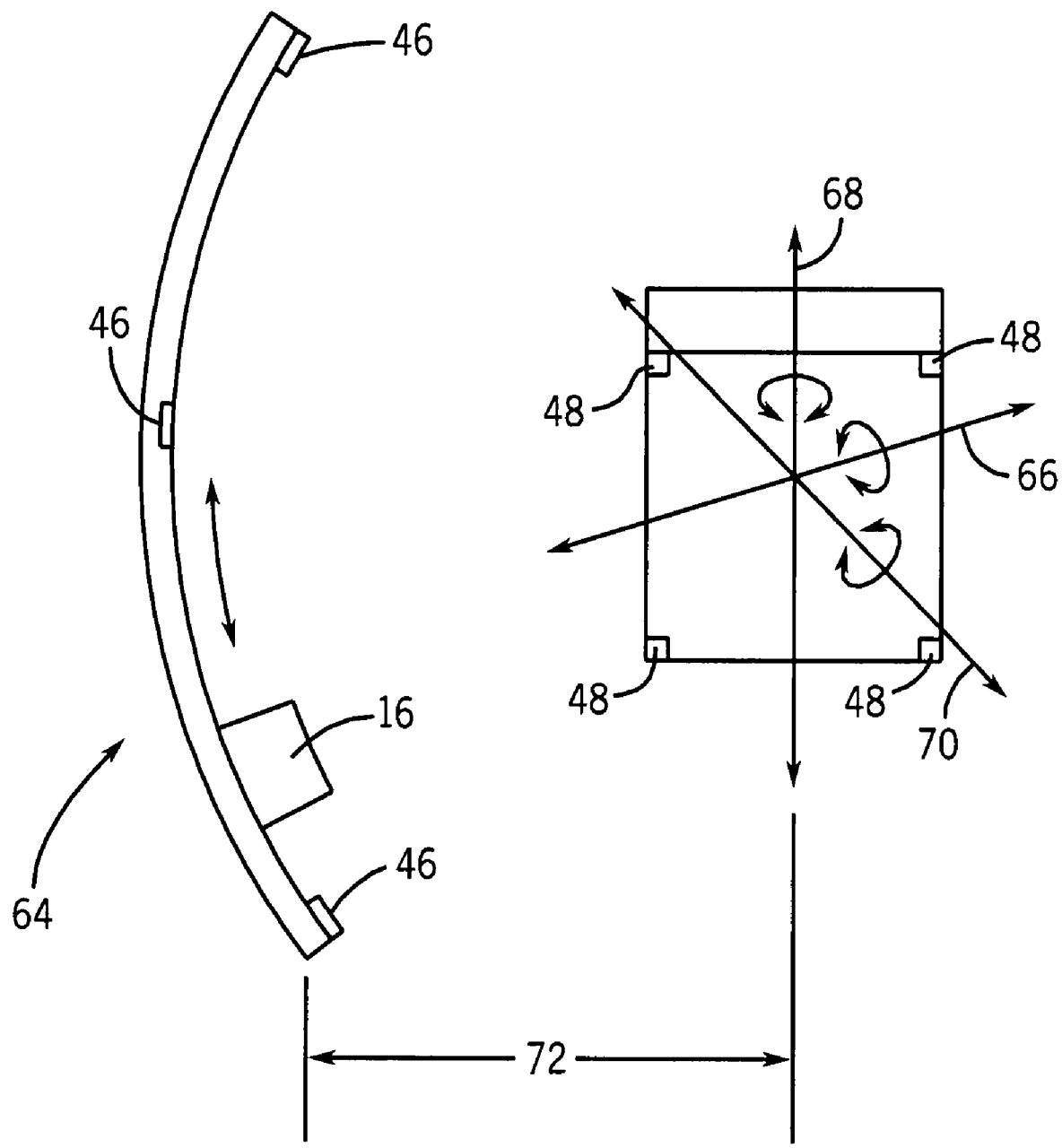
Figure 5:
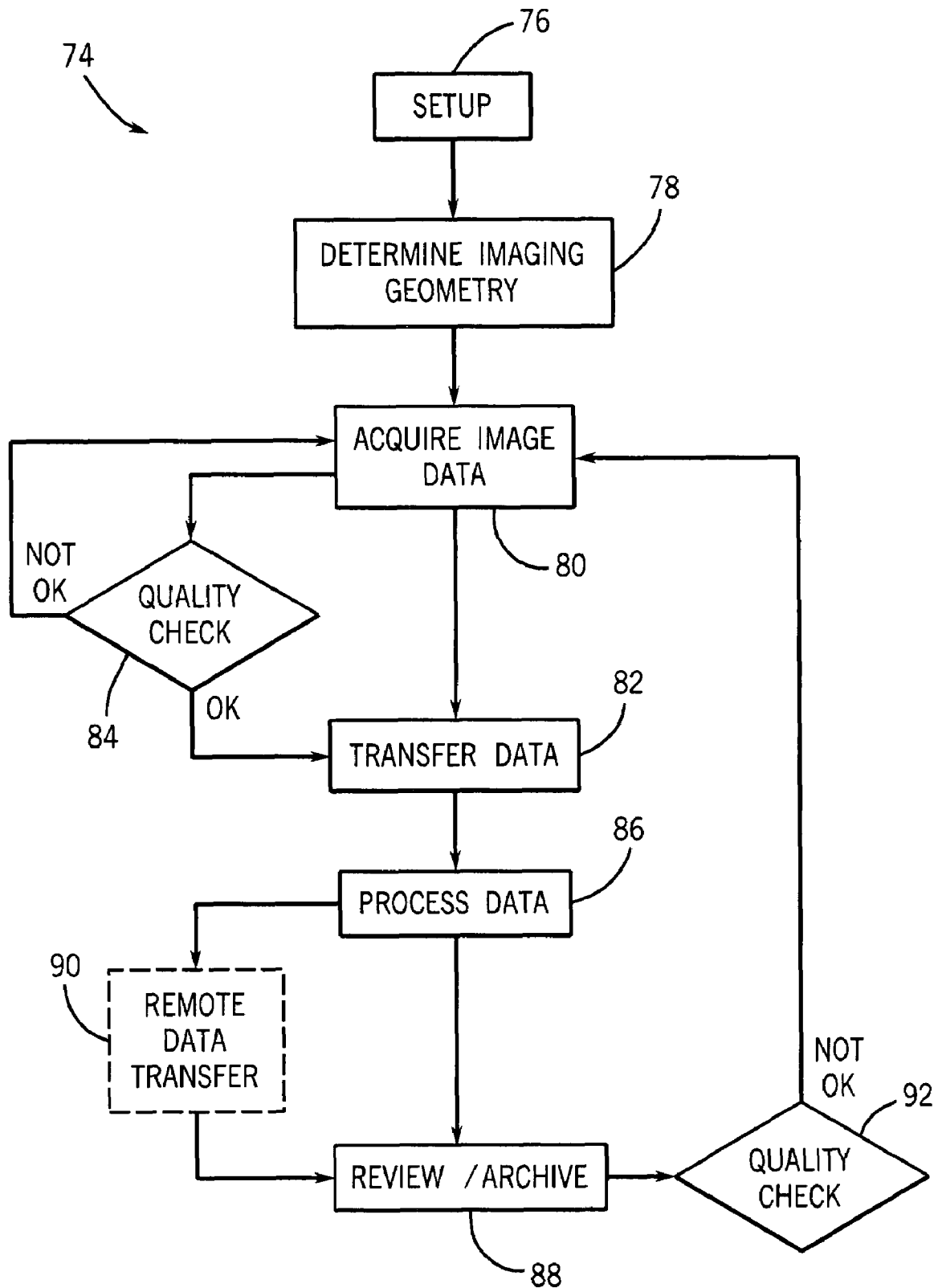

FIG. 4 is a diagrammatical representation of a non-linear track for a moveable X-ray source, and also illustrating a presently contemplated manner for determining the position and orientation of the source and detector with respect to one another; and FIG. 5 is a flow chart illustrating exemplary logic for carrying out imaging via a portable or displaceable tomosynthesis imaging system in accordance with the invention.

DETAILED DESCRIPTION

Figure 1:
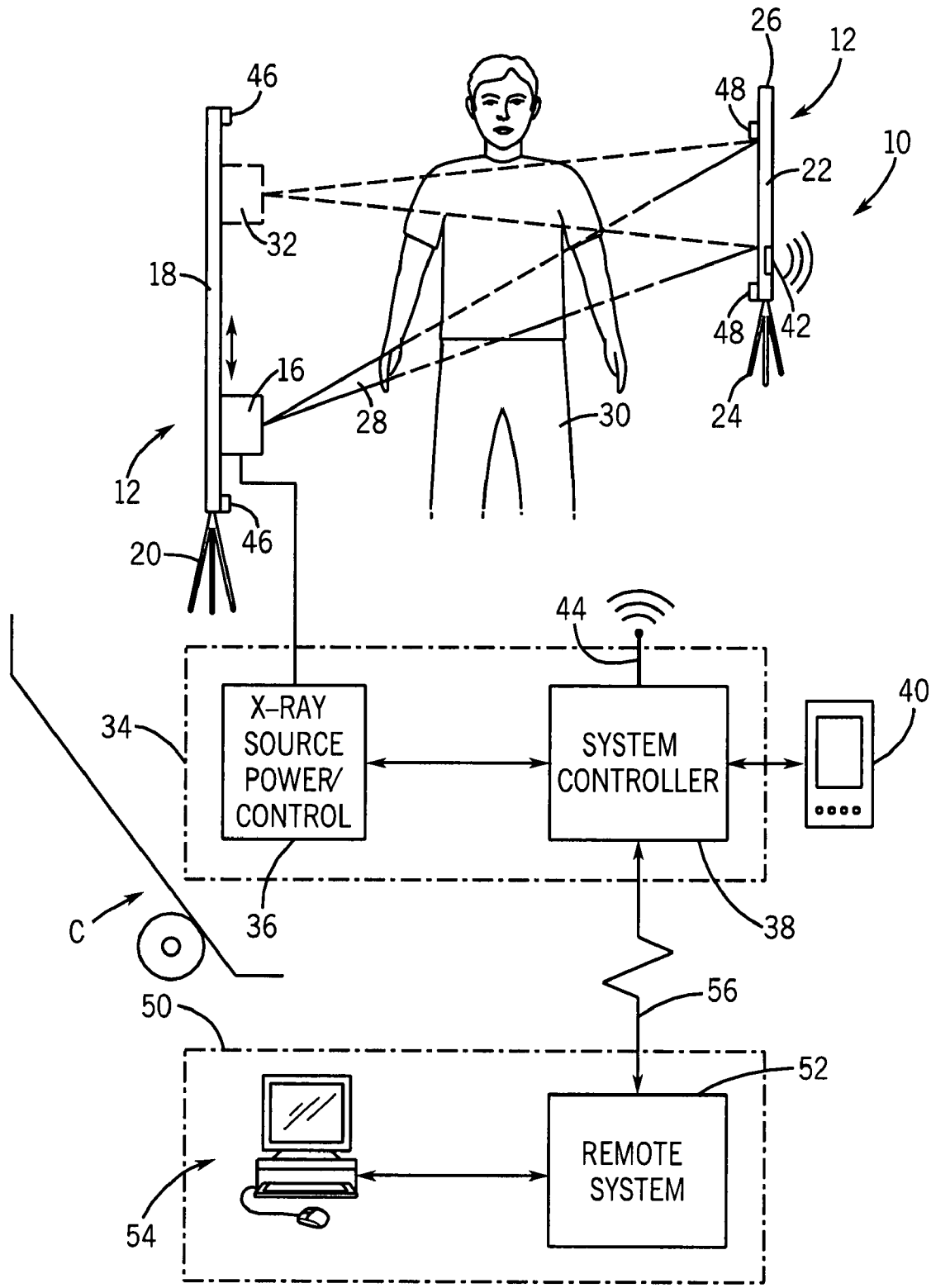
FIG. 1 is a diagrammatical overview of a portable tomosynthesis system in accordance with aspects of the present technique.

Turning now to the drawings, and referring first to FIG. 1, a portable tomosynthesis system is illustrated diagrammatically and represented generally by reference numeral 10. The system includes a portable X-ray source assembly 12 designed to cooperate with a portable detector assembly 14 to generate a series of projection images that can be used for calculating slice images through a subject of interest. In the illustrated embodiment, the source assembly 12 includes a moveable X-ray source 16 designed to slide or be drawn along a support 18. The source will typically move along a track formed in the support 18, and may move along linear or non-linear paths as discussed in greater detail below. In a presently contemplated embodiment, the source assembly 12 may include some sort of mechanical mounting structure 20, such as a tripod which can be deployed and collapsed for ease of movement and storage of the source assembly.

The detector assembly 14 may be physically separate from the source assembly as in the illustrated embodiment. The detector assembly will include a digital X-ray detector 22, also associated with mechanical mounting structures 24, where appropriate. In presently contemplated embodiments, for example, the mechanical mounting structure 24 may include a tripod assembly similar to that used for the source assembly. In certain settings, however, this mounting structure may be eliminated or removable, such as for manually holding the detector or positioning the detector in tight or confined locations, such as in an accident scene or trauma location where a patient is not to be moved. The detector itself may be generally similar to conventional digital X-ray detectors, including a scintillator for converting X-ray radiation to lower energy photons, photodiodes for receiving the photons from the scintillator, and transistors for reading out the charge depletion in the photodiodes resulting from the impacting photons. Such circuitry will typically be included within the detector package itself. Moreover, the detector assembly may also include a battery pack 26, particularly where the detector is not powered by a separate power supply as in the illustrated embodiment. Of course, separate power supplies may be provided for the detector, and these would be linked to the detector by appropriate power cables.

During operation, the source 16 emits a beam of radiation 28 that is directed to a region of interest within a patient 30. The radiation traverses the subject and impacts the detector 22 where data can be collected corresponding to a digital X-ray projection from the source location. As will be appreciated by those skilled in the art, the source 16 itself will typically include an X-ray tube, radiation shielding, and a collimator which forms the beam 28 and directs the beam towards the detector. The source may also include one or more motors or other positioning devices which allow for directing the beam appropriately to the detector. Similarly, the source may include a motor that is controlled to draw the source along the support 18 between projection image locations. As with conventional tomosynthesis systems, the source may be moved in a continuous manner or in a "step-and-shoot" mode. Alternatively, a separate motor and transport assembly may be provided on the support 18, to draw the X-ray source between the desired imaging positions. Two such imaging positions, designated by reference numeral 32, are illustrated in FIG. 1.

The X-ray source 16 is coupled to a portable power supply and control system 34, as is the detector 22. The power supply and control system provides control signals for operation of the X-ray source for its movement, and for triggering image acquisition by emission of X-rays from the source. The system also coordinates the acquisition of image data from the detector. In the illustrated embodiment, the portable power supply and control system 34 includes an X-ray source power supply and controller 36 and a system controller 38. These may include one or more programmed computers or application-specific processors designed to implement the imaging protocols, and to control the source and detector. Specifically, the X-ray source power supply and controller 36 may be coupled to the X-ray source by a power cable and may, itself, include a battery bank and/or cords for drawing power from a generator, battery, emergency vehicle, or other source, including the power grid when the system is located in the vicinity of utility outlets.

The system controller 38 may command operation of the X-ray source power supply and controller 36, or at least coordinate the movement and energization of the source with image acquisition by the detector. In the illustrated embodiment, the system controller 38 is coupled to a portable viewer or interface 40. Such interfaces may be, for example, specially designed human interface modules, laptop computers, tablet computers, personal digital assistants, and so forth. The interface may be hard-wired to the system controller, or may be coupled to the controller wirelessly. In general, it is contemplated that the viewer or interface 40 will permit personnel local to the portable tomosynthesis system to determine whether satisfactory images are being obtained, to interface with the system for launching image acquisition, viewing and configuring parameters of the source and detector, and so forth.

As also illustrated in FIG. 1, in a presently contemplated embodiment the detector assembly 14 may be wirelessly coupled to the control system 34 for transmitting image data and commands between these components. Thus, the detector assembly may include a transceiver 42 while the system controller 38 may include similar transceiver 44. The transceivers may function in accordance with any desired wireless transition protocols, such as Blue tooth, infrared protocols, IEEE 802.11, and so forth. In general, the system controller will prompt the detector to send image data, after which the image data stored in the detector will be transmitted frame-by-frame. This may be done during image acquisition, or post-acquisition. Where the image data is transmitted from the detector assembly wirelessly, the detector assembly will typically include one or more memory devices that at least temporarily store the image data for transmission in accordance with the desired wireless protocol. Where the detector and the system controller are coupled to one another by wiring cables (not shown) the transmission of data may be prompted by the system controller or may be performed as in conventional clinical tomosynthesis systems during image acquisition.

As will be appreciated by those skilled in the art, for reconstruction of tomosynthesis images based upon the projection images acquired via the portable X-ray source assembly and the portable detector assembly, the position of the source assembly with respect to the detector assembly is generally to be known. However, because the source assembly and the detector assembly as physically separate from one another, in a presently contemplated embodiment illustrated, each are equipped with orientation sensors 46 and 48. These orientation sensors may function in accordance with a range of different physical principles. However, in the presently contemplated embodiment, these sensors are electromagnetic transceivers, or separate transmitters and receivers that create and sense electromagnetic fields. That is, if the orientation sensors 46 on the source assembly are transmitters, the sensors 48 on the detector may be receivers that sense the fields emitted by the sensors 46. Because the exact locations of the orientation sensors 46 on the source assembly are known, as are the relative positions of the sensors with respect to one another, as are the locations and the relative positions of the sensors 48 on the detector assembly, the sensed fields can be used to determine the distance of the detector from the sensor, as well as the relative orientation of the these components with respect to one another as described more fully below. In practice, one or both of the source assembly and detector assembly may include both transmitters and receivers, or the sensors on both of these devices may be configured to operate as both transmitters and receivers. In some implementations, one of the devices may be equipped with transmitters and the other with receivers, as discussed above. In general, the sensed information is stored either in the source assembly or the detector assembly, and is then transmitted through the system controller for use in the reconstruction of the three-dimensional tomosynthesis images.

The reconstruction of the slices or planes of these tomosynthesis images may be performed in the portable power supply and control system 34 or in remote facilities and systems. In the embodiment illustrated in FIG. 1, for example, the portable system 34 is coupled to a remote facility 50 which includes a remote system 52, typically in imaging or image processing system, and a workstation, interface or viewer 54. The remote system can receive image data, orientation data, and so forth, via an appropriate network link 56, such as including the Internet, wireless links, satellite links, and so forth.

Image reconstruction may follow protocols similar to those used for conventional tomosynthesis imaging. That is, as will be appreciated by those skilled in the art, backprojection, filtered backprojection or other known resonstruction techniques may be employed, with the particular position of the source with respect to the detector being determined by knowledge of the position of the source along the support 18, and knowledge of the relative orientations and distances between the source assembly 12 and the detector assembly 14 computed based upon the fields sensed by the transceivers 42 and 44. Where images are produced by the portable system itself, these slices may be viewed on the viewer or interface 40 local to the system. Alternatively, the viewer or interface 40 may be used to view projection images generated by the system, but not tomosynthesis images. The reconstructed tomosynthesis images may be transmitted to the remote system 52, or raw or filtered image data may be transmitted and the actual reconstruction of the tomosynthesis images may be performed remotely to the exclusion of the portable system, where desired.

As noted above, the system control circuitry may command such parameters as movement of the X-ray source, initiation of exposures, acquisition of data, transfer of data, and so forth. Moreover, the control circuitry may regulate source exposure times, directions of the X-ray beam, where possible, and so forth. Similarly, where the orientation transceivers indicate that reliable image information may be obtained with the current positioning of the source assembly and detector assembly, a visual or audible indication of this may be provided to an operator. Conversely, an audible or visual indication that the positioning is not conducive to producing good image quality (based upon particular system design limits), may also be provided. This may be done at the location of the detector, the source or the portable system 34. Similar indications may be provided by the viewer or interface 40. With this type of indication, an operator may be notified that repositioning of either the source assembly or the detector assembly, or both, may be desired to produce the desired image quality.

FIG. 1 diagrammatically illustrates that the entire system shown may be transported to different locations via a carrier C. In general, and as mentioned above, the system is particularly designed for ready transport to various improvised or temporary medical care locations, such as accident scenes, trauma locations, field medical care centers, and so forth. However, is should also be borne in mind that the system is designed for use in non-permanent locations or positions within clinics, hospitals, and so forth. Thus, as used herein, the term "portable" connotes the ability to move the system between non-dedicated imaging locations. Thus, the term is not intended to include systems that are permanently or semi-permanently installed in imaging rooms or departments of hospitals or clinics. It also is not intended to mean truck, van or bus-based (i.e., vehicular-based) systems. The carrier C, or equivalent transport means, then, might include one or more packs, cases, wheeled carts, and so forth. Depending upon the size and weight of the components (particularly the X-ray source assembly and the power supply), more than one such carrier will typically be required.

Figure 2:
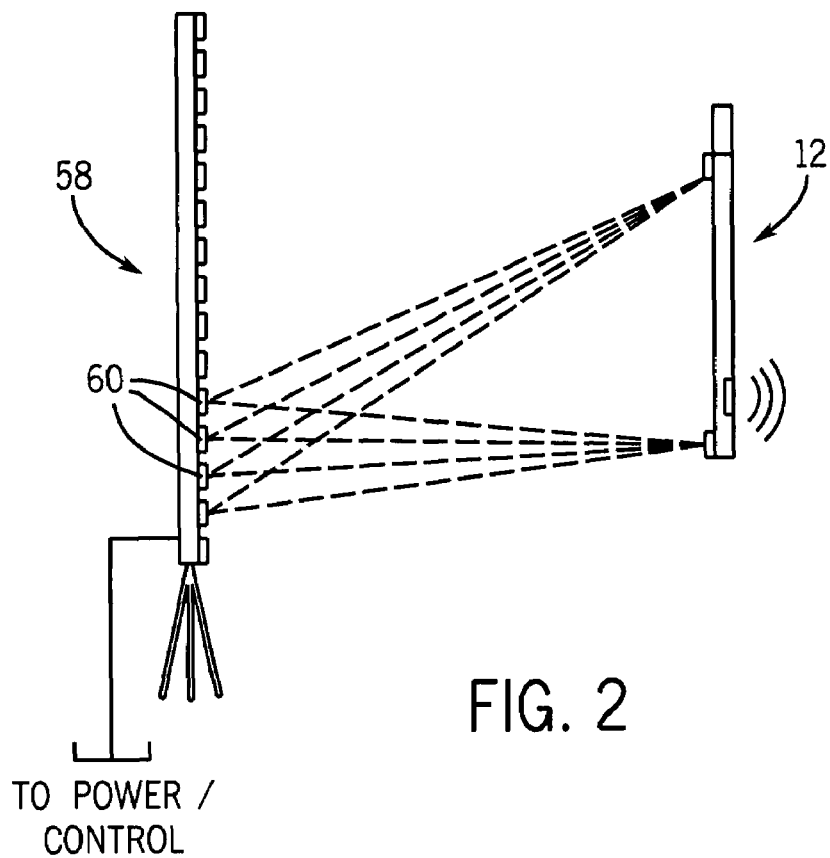
FIG. 2 is a diagrammatical representation of a distributed source that may be used in the tomosynthesis system of FIG. 1.
Figure 3:
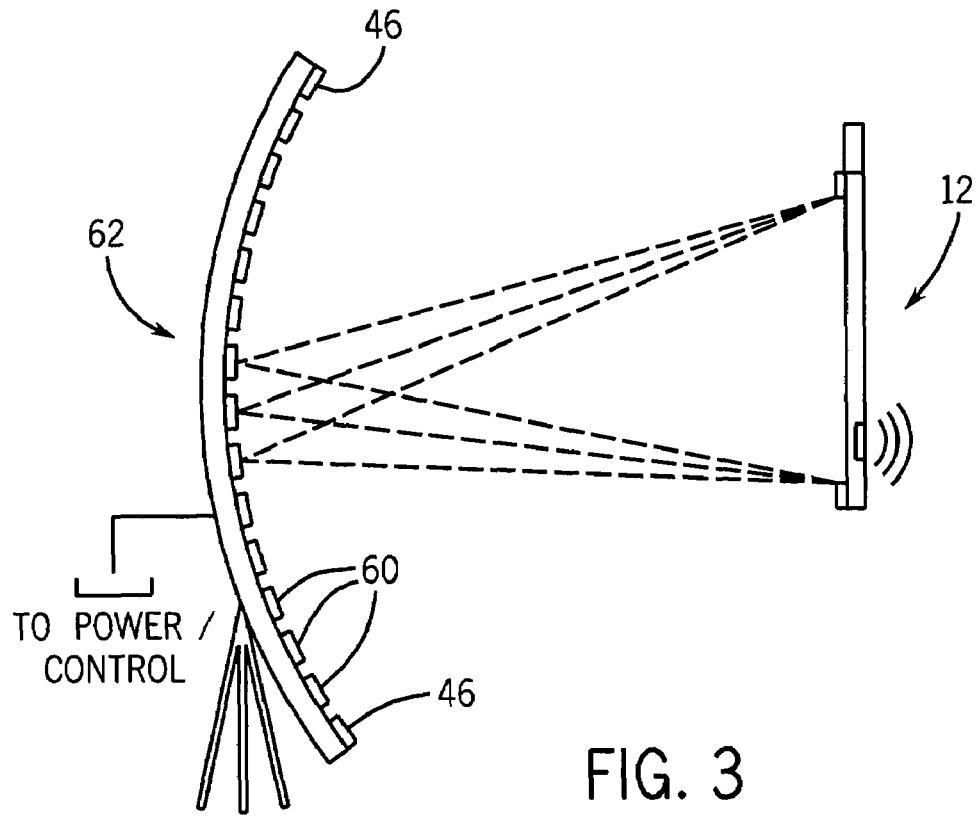
FIG. 3 is a similar diagrammatical illustrated of a non-linear distributed X-ray source that may be used in the portable tomosynthesis system.

Alternatives to the foregoing implementation may include source assemblies made up of a plurality of distributed sources, such as those illustrated in FIGS. 2 and 3. In FIGS. 2 and 3, the system controller, power supplies, and so forth have not been shown for the sake of simplicity. As illustrated in FIG. 2, for example, a distributed source 58 may include a plurality of X-ray sources 60, such as field emitter devices, or other controllable and addressable X-ray sources. The sources may be aligned along a support of the type illustrated in FIG. 1, and these may be supported mechanically by a tri-pod or other mechanical support structure as described above. Other features of the system may be essentially similar to those described above, with orientation of the source assembly and detector assembly again being determined during imaging to permit reconstruction of the desired tomosynthesis slices based upon multiple X-ray projection images.

FIG. 3 illustrates another presently contemplated distributed source, which in this case is a non-linear source assembly 62. As in the source 58 of FIG. 2, the distributed source assembly 62 has multiple individual X-ray sources, such as field emitter devices arranged along a non-linear path. In general, such non-linear paths may be used to ensure that the radiation is directed appropriately to the detector plane, or to correct for magnification changes if these components are not parallel. In a simple implementation, for example, this may involve the use of spirit levels or goniometers mounted to both the source and detector. Moreover, in the embodiments of FIGS. 2 and 3, the source can be collimated, as with the moveable source implementation, to provide certain beam shape exposing the detector in particular regions of interest, or fields within the detector array. The separation between different X-ray generation points along the source is generally sufficient to produce the desired tomosynthesis images.

The use of arcuate or other curve shapes for the source positions may be desirable over linear arrays for various reasons. Such curve linear source positions may have the advantages of reducing the conspicuity of tomosynthesis "ripple" artifacts without increasing the mechanical complexity as would be the case with a conventional source. Another implementation could utilize two linear arrays in a cross shape to reduce the conspicuity of tomosynthesis ripple artifacts. A combination of two linear arrays that would then be assembled on site into a cross or other configuration would have the advantage of simplifying the production and transportation of the source as compared to an arc configuration.

FIG. 4 represents a similar arcuate or non-linear support 64 on which a moveable X-ray source 16 is positioned. Again, the support is equipped with transceivers 46 that assist in determining the distance and orientation of the source assembly with respect to the detector assembly. FIG. 4 illustrates the detector assembly in a front elevational view, although in use the detector assembly would be positioned generally parallel to the plane or parallel to the cord of the arcuate source path. The detector assembly is so positioned in FIG. 4 for explanatory purposes, that is, to illustrate that the detector assembly, by virtue of the transceivers 46 and 48, may be located in space along three orthogonal axes 66, 68 and 70 in space. Moreover, the orientation of the detector, determined by rotation about any one or more of these axes may also be determined. For such determinations, it may be desirable to provide three or more transceivers on both the source assembly and the detector assembly to allow calculation of the geometrical transforms needed to precisely locate the source with respect to the detector during the period in which the individual projection X-ray images are produced. The distance 72 may also be computed, and all of these parameters may be used to determine whether positioning is appropriate for good image quality, or whether repositioning may be in order.

FIG. 5 illustrates exemplary logic for performing imaging on a portable or displaceable imaging system of the type described above. The process, is designated generally by reference numeral 74, begins with a set-up step at block 76. In general, the setup step will include transportation or displacement of the imaging system to the desired location, such as an accident scene, a trauma scene, a non-regular medical installation, a field medical installation, and so forth. The setup will typically include unpacking of the portable source assembly and the detector assembly and connection of the source assembly to the power supply. Other setup may include connection of various cables, such as to an interface where provided. Links between wireless devices may also be verified, as well as network links to remote devices to which image data will be transmitted.

At step 78 the imaging geometry is determined. In general, this may include sending and receiving signals between sensors, transmitters, receivers or transceivers on the source assembly and detector assembly to verify the position, orientation, alignment and so forth of these with respect to one another. As noted above, the alignment may be verified and alarms or other feedback may be provided to an operator to facilitate the alignment and the appropriate geometry for tomosynthesis imaging. At step 80, then, the system may be controlled to acquire image data. As noted above, and as will be appreciated by those skilled in the art, the tomosynthesis imaging process generally includes the capture of a series of projection images during either displacement of a moveable X-ray source or triggering of distributed sources, or both. The image data is captured by sampling of pixel circuitry in the detector, and processing of the resulting signals, such as by analog-to-digital conversion, scaling, and so forth.

As indicated at step 82, the image data is ultimately transferred from the detector to the control and processing components of the system. However, in parallel with this transfer, or even before the transfer, a quality verification may be performed as indicated at step 84. This quality check may include the evaluation of the image data, as well as relationships between the image data to determine whether sufficient integrity of the data is present for permitting the reconstruction of tomosynthesis images. The quality check may also include verification that the system has not moved to a degree that makes reconstruction of the images impossible. Other quality checks on the system and the collected image data may also be performed at this phase of the procedure. If the image quality is found to be lacking, the process may return to step 80 where images are re-acquired, similarly processed, stored and ultimately transferred at step 82 once sufficient image quality is obtained.

At step 86, then, the image data may be processed. The processing may include actual reconstruction of tomosynthesis slices that may be viewed locally on an interface of the type described above. It should also be noted that the quality check at step 84 may include human verification of image quality, such as via this local interface. The image data may also be processed at step 86 to permit raw, partially-processed or fully-processed images or tomosynthesis slices to be stored and sent to remote locations. Once satisfactory images are obtained, therefore, a review and archive step 88 may be performed for both utilization of the images for clinical, diagnostic and other purposes, as well as the ultimate storing of the images for later reference.

As indicated at step 90, the image data, including raw, partially-processed and fully-processed image data may be sent to remote locations. Such locations may typically include remote hospitals, surgical centers, universities, and so forth where a specialist may be present to evaluate the need for particular medical care. Based upon such evaluations, feedback may be provided to the clinical team operating the portable system to guide the rendering of medical care, the transport of a patient, and so forth.

As noted at step 92 in FIG. 5, a further quality check may be performed at this stage. The quality evaluation at step 92 may be essentially similar to that performed at step 84, although such quality checks may actually be performed on processed data, reconstructed images, and so forth. The quality check performed at step 92 may be performed partially or fully at a remote location to which the image data is transferred. Based upon such evaluation, the processing may return to step 80 where additional images are acquired to permit better evaluation of the need for medical attention. The provision of step 92 in a real-time or near real-time processing of the image data, and the performance of quality checks, is particularly attractive insomuch as this may permit remote specialist to evaluate the need to acquire additional image data before a patient is moved, medical treatment is administered, or, more generally, while an emergency situation exists requiring imaging. In other contexts, such as in clinical settings where the imaging system is at least temporarily positioned, the quality check at either step 84 or at step 92 may permit appropriate high-quality imaging while a patient is still present in a clinical or other facility. This may avoid the need to recall the patient for subsequent imaging.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A portable tomosynthesis imaging system comprising:
   a portable X-ray source assembly configured to direct X-ray radiation towards a subject from a plurality of different source positions;
   a portable digital detector assembly configured to receive the radiation from the source and to remain stationary during receipt of the radiation from the plurality of different source positions;
   a portable power supply for powering the X-ray source assembly;
   control circuitry coupled to the X-ray source assembly and to the detector assembly and configured to control acquisition of projection image data sets for the plurality of different source positions for reconstruction of tomosynthesis images; and
   means for transporting the source assembly, detector assembly, power supply and control circuitry to a non-dedicated imaging location;
   wherein the X-ray source assembly and the detector assembly are separately mounted on separate support structures; and
   wherein the X-ray source assembly and the detector assembly include sensors and/or transmitters cooperatively arranged to detect distance and orientation of the source assembly and detector assembly with respect to one another.

2. The system of claim 1, wherein the X-ray source assembly includes a moveable source mounted to a support along which the source moves.

3. The system of claim 2, wherein the support is generally linear.

4. The system of claim 1, wherein the X-ray source assembly includes a plurality of distributed sources mounted along a support.

5. The system of claim 4, wherein the support is generally linear.

6. The system of claim 1, wherein the detector is wirelessly coupled to the control circuitry for transmitting image data to the control circuitry and/or control signals from the control circuitry to the detector.

7. The system of claim 1, further comprising a portable human interface device coupled to the control circuitry.

8. The system of claim 7, wherein the portable human interface device is wirelessly coupled to the control circuitry.

9. The system of claim 1, wherein the control circuitry is configured to compute tomosynthesis images based upon the projection image data sets.

10. The system of claim 1, wherein the control circuitry is configured to transmit the projection image data sets to a remote system for computation of tomosynthesis images.

11. The system of claim 1, wherein the source positions form an angle of between approximately 5 and 120 degrees with respect to the detector.

12. The system of claim 1, wherein the source positions form an angle of between approximately 20 and 40 degrees with respect to the detector.

13. A portable tomosynthesis imaging system comprising:
a portable X-ray source assembly configured to direct X-ray radiation towards a subject from a plurality of different source positions, wherein the source positions form an angle of between approximately 5 and 120 degrees with respect to a detector;
a portable digital detector assembly configured to receive the radiation from the source and to remain stationary during receipt of the radiation from the plurality of different source positions, wherein the X-ray source assembly and the digital detector assembly are separately mounted on separate support structures;
means for detecting distance and orientation of the source assembly and detector assembly with respect to one another;
a portable power supply for powering the X-ray source assembly;
control circuitry coupled to the X-ray source assembly and to the detector assembly and configured to control acquisition of projection image data sets for the plurality of different source positions for reconstruction of tomosynthesis images; and
at least one carrier for transporting the source assembly, detector assembly, power supply and control circuitry to a non-dedicated imaging location.

14. The system of claim 13, wherein the source positions form an angle of between approximately 20 and 40 degrees with respect to the detector.

15. A tomosynthesis imaging system for generating tomosynthesis image data at a non-dedicated imaging location comprising:
an X-ray source assembly configured to direct X-ray radiation towards a subject from a plurality of different source positions;
a digital detector assembly configured to receive the radiation from the source;
a power supply for powering the X-ray source assembly;
means for detecting positions of the source assembly and detector assembly with respect to one another and for generating position data representative thereof;
control circuitry coupled to the X-ray source assembly and to the detector assembly and configured to control acquisition of projection image data sets for the plurality of different source positions for reconstruction of tomosynthesis images based upon the projection image data sets and the position data; and
means for transporting the source assembly, the detector assembly, the power supply, the means for detecting positions and the control circuitry to a non-dedicated imaging location.

16. A method for generating tomosynthesis images at a non-dedicated imaging location comprising:
positioning a portable X-ray source assembly adjacent to a subject, the source assembly being configured to direct X-ray radiation towards a subject from a plurality of different source positions;
positioning a portable detector assembly adjacent to the subject opposite the source assembly, the detector assembly being configured to receive the radiation from the source and to remain stationary during receipt of the radiation from the plurality of different source positions, wherein the X-ray source assembly and the detector assembly are separately mounted on separate support structures;
detecting distance and orientation of the source assembly and detector assembly with respect to one another;
coupling a portable power supply to the X-ray source assembly; and
commanding operation of the source assembly and the detector assembly via a portable controller to control acquisition of projection image data sets for the plurality of different source positions for reconstruction of tomosynthesis images.

17. The method of claim 16, further comprising generating an audible or visible signal to advise an operator of alignment or orientation of the source assembly and detector assembly.

18. The method of claim 16, comprising reconstructing a tomosynthesis image in the portable controller based upon the projection image data sets.

19. The method of claim 16, comprising transmitting the projection image data sets to a remote location for reconstruction of a tomosynthesis image.

20. A method for generating tomosynthesis images at a non-dedicated imaging location comprising:
positioning a portable tomosynthesis system at a non-dedicated imaging location, the system including an X-ray source and a digital detector separately mounted on separate support structures;
verifying alignment of the X-ray source of the system with the digital detector by detecting distance and orientation of the source assembly and detector assembly with respect to one another;
acquiring image data via the system;
performing a quality verification of the image data; and
optionally reacquiring image data based upon the quality verification.

21. The method of claim 20, comprising adjusting a position of the X-ray source or the detector or both prior to reacquiring the image data.

22. The method of claim 20, wherein the alignment is verified based upon signals exchanged between a transmitter on one of the X-ray source and the detector, and a receiver on the other of the X-ray source and the detector.

23. The method of claim 20, comprising transferring the image data or an image derived from the image data to a remote location.

24. The method of claim 20, wherein the quality verification is performed locally at the tomosynthesis system.

* * * * *